United States Patent [19]

Person

[11] 3,999,555
[45] Dec. 28, 1976

[54] ATRIAL PINCH ON LEAD AND INSERTION TOOL

[75] Inventor: Gerald C. Person, Blaine, Minn.

[73] Assignee: Medtronic, Inc., Minneapolis, Minn.

[22] Filed: Oct. 28, 1975

[21] Appl. No.: 626,429

[52] U.S. Cl. .............................. 128/418; 128/321; 128/419 P

[51] Int. Cl.$^2$ .......................................... A61N 1/04

[58] Field of Search ............... 128/418, 404, 419 R, 128/2.06 E, 2.1 E, DIG. 4, 346, 326, 321, 325, 337, 354

[56] References Cited

UNITED STATES PATENTS

| | | | |
|---|---|---|---|
| 3,120,227 | 2/1964 | Hunter, Jr. et al. | 128/2.06 E |
| 3,175,556 | 3/1965 | Wood et al. | 128/326 |
| 3,326,217 | 6/1967 | Kerr | 128/325 |
| 3,800,784 | 4/1974 | Kiszel et al. | 128/2.06 E |
| 3,867,944 | 2/1975 | Samuels | 128/346 |
| 3,916,908 | 11/1975 | LeVeen | 128/346 |

FOREIGN PATENTS OR APPLICATIONS

| | | | |
|---|---|---|---|
| 1,575,665 | 6/1969 | France | 128/419 P |
| 1,030,556 | 5/1966 | United Kingdom | 128/337 |
| 636,853 | 5/1950 | United Kingdom | 128/354 |

OTHER PUBLICATIONS

Hon, "Instrumentation . . . Fetal ECG," Am. J. Obst. & Gynec., vol. 86, No. 6, July 15, 1963, pp. 772–784.
Hon, "Instrumentation . . . Fetal ECG, III Fetal ECG Electrodes" Obst. & Gynec., vol. 30, No. 2, Aug. 1967, pp. 281–286.
Kopernik, "Die Ableitung . . . Skalpelektrode," Dtsch. Gesundheitswesen, 26: 1756–1759, Sept. 9, 1971.
Copland et al., "A Simple Clinical Skin Electrode," The Lancet, No. 7330, vol. 1, p. 416, 2/22/64.

Primary Examiner—Robert W. Michell
Assistant Examiner—Lee S. Cohen
Attorney, Agent, or Firm—Joseph F. Breimayer; Irving S. Rappaport

[57] ABSTRACT

A body implantable lead and insertion tool for attaching the lead to an internal body organ. The lead carries an electrode having first and second spaced organ engaging pincers. The insertion tool comprises jaws for firmly grasping the first and second spaced organ engaging pincers for facilitating the attachment thereof to a fold of the internal organ between the pincers. The pincers may be mechanically deformed to a closed position through opposing sides of the body organ fold by the application of a mechanical deforming force to and through the insertion tool. The tool also has a stop member for limiting the deformation of the first and second spaced organ engaging pincers to a predetermined extent.

12 Claims, 5 Drawing Figures

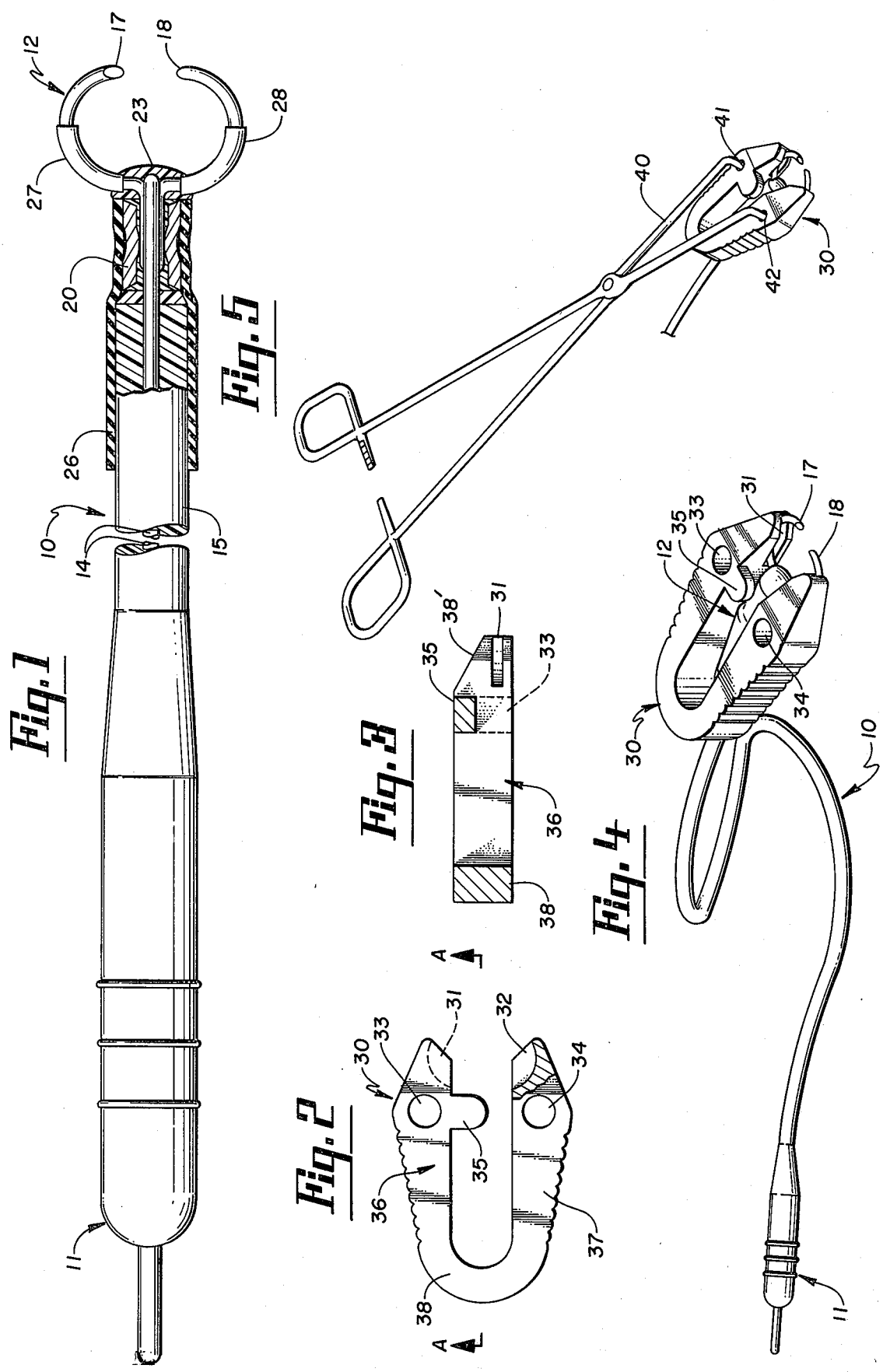

ATRIAL PINCH ON LEAD AND INSERTION TOOL

BACKGROUND OF THE INVENTION

The positive securement or attachment of electrodes to internal body organs has been accomplished in several ways. With respect to the heart, for example, electrode placement and attachment has been effected transvenously as well as transthoracically.

The transvenous approach has as its purpose an electrical contact with or into the endocardium by extension of the lead through the vein system of the heart to the output terminals of an implanted pulse generator. Dependent upon the purpose of the contact, the desired position of the electrode may be within the ventricle, atrium, or atrial appendage of the heart. Positioning is accomplished through the use of fluoroscopy, or other similar techniques, and is an inexact art, at best. Attachment often is not positive in that the electrode is positioned at a reasonably stable position, e.g., the right atrial appendage in the hope that the electrode will remain in position until it is secured through a natural buildup of fibrotic tissue. In an effort to hold the electrode in position pending the buildup of fibrotic tissue, some prior art transvenous electrodes have been provided with mechanical devices for engagement with the heart tissue, particularly the trabeculae of the right atrial appendage. Such a prior art transvenous electrode is disclosed in U.S. Pat. No. 3,902,501.

The transthoracic approach has as its purpose a positive epicardial or myocardial electrical contact. The configuration of most prior art electrodes of this type required a thoracotomy for positioning and attachment, particularly to the atrium or atrial appendage. The sutureless myocardial lead disclosed in U.S. Pat. No. 3,737,579 has its primary application to the ventricular attachment. The atrium for the most part is relatively thin-walled and incapable of accepting the sutureless myocardial lead. The exterior of the atrial appendage is rather convoluted and does not afford an acceptable surface or angle of approach for this lead.

From the above, it can be seen that the more accurate positioning and positive securement available with a thoracotomy carries with it a much greater patient risk. While the risk to the patient is significantly less with a transvenous approach, the positioning of the electrode and its securement are much less certain.

SUMMARY OF THE INVENTION

The present invention provides an electrode and an electrode insertion tool which allows the precise positioning and positive attachment to the heart heretofore attainable only through a thoracotomy while eliminating the need for the thoracotomy. There is no need to break or separate ribs, and the placement may be effected with a local anesthetic. Surgical time is also reduced which lessens patient morbidity. These and other features of the present invention make treatment available to people who would otherwise be rejected as unsuitable candidates for thoracotomy.

The present invention comprises a lead with an electrode having first and second spaced organ engaging pincers. The electrode is adapted to receive a fold of a body organ between the pincers and to be mechanically deformed through the opposing sides of the body organ fold. A lead insertion tool having a pair of pincer engaging jaws is provided for positioning and deforming the pincers described. The insertion tool allows positioning of the electrodes from above or below the rib cage or through the rib cage with a limited thoracotomy and, with a judicious selection of the point of ingress, the positioning and attachment may be directly observed.

The electrode configured for engagement with the right atrial appendage which possesses a fold-like configuration. When placement on the atrium, ventricle or a portion of another body organ is desired, it may be necessary to mechanically create a fold with which the electrode can engage. In either instance, an electrode built in accordance with the present invention is less likely to tear the body organ tissue than suturing techniques previously employed.

It has been found that a positive attachment of the electrode requires that it puncture the organ to which it is to be applied and for that purpose, the electrode is provided with cutting surfaces at the termini of the pincers. It has also been found that ends of the pincers should at least touch in the deformed position and may overlap to provide the most positive securement.

The electrode is also uniquely configured for gripping engagement by grooves located in opposite surfaces of the jaws of the insertion tool of the present invention. The insertion tool itself includes means adapted to be engaged by an ordinary operating room instrument, such as a right angle forceps. The insertion tool securely holds the electrode pincers and in turn the forceps securely hold the insertion tool. In this manner, it is unlikely that the electrode will accidentally slip during the insertion procedure. The electrode is extremely easy to position and attach in view of the action of the insertion tool.

The insertion tool is relatively small and in conjunction with a forceps allows for the use of a limited thoracotomy. The lack of slippage at the moment of attachment of the pincers of the electrode to the fold of the body organ reduces the danger of injury to the body organ and distortion of the pincers. A secure and uniform attachment of the pincers to the fold of the body tissue is thus effected.

With these advantages and features of the invention, as will hereinafter more fully appear in mind, reference is now made to the following description taken in connection with the accompanying drawings.

DESCRIPTION OF THE DRAWINGS

FIG. 1 shows a partial cutaway view of an implantable lead in accordance with the present invention;

FIG. 2 is a partial cutaway plan view of a preferred embodiment of the insertion tool of the present invention;

FIG. 3 is a cross section of the preferred embodiment of the insertion tool of FIG. 2 taken along the line A—A;

FIG. 4 is a view in perspective illustrating the lead of FIG. 1 and the insertion tool of FIGS. 2 and 3 in operative relationship with one another; and FIG. 5 is a further perspective view illustrating the operative relationship of the insertion tool and lead of FIG. 4 with a conventional right angle forceps in preparation for attachment of the lead to a body organ.

DESCRIPTION OF THE PREFERRED EMBODIMENT

FIG. 1, which illustrates a preferred embodiment of the lead of the present invention, shows a lead 10 originating at a connector portion 11 and terminating an electrode 12. The connector portion 11 is of the type commonly referred to as pin form and is illustrative only, any connector configuration capable of efficiently making contact with a remote electrical device, such as a pulse generator, being sufficient.

Between the connector portion 11 and electrode 12 is a conductor 14 encased in an insulating material 15 which is generally inert to body fluids and tissues. The conductor 14 may be of any type known in the art and may comprise braided, coiled, tinsel wire or otherwise. Again the particular construction and composition of the connector portion 11, conductor 14 and insulating material 15 is known to the prior art in forms a part of the present invention only in combination with the electrode 12.

The electrode 12 is composed of a first arcuate pincer 17 whose free end is in spaced opposing relation to the free end of a second arcuate pincer 18. In the embodiment of FIG. 1, the pincer 17 and 18 are generally semi-circular and may comprise a single length of rod or wire bent at its midpoint in the configuration shown. The conductor 14 contacts the pincers 17 and 18 at the midpoint. Electrical and mechanical connection is maintained by use of conductive epoxy at the contact point. In a preferred embodiment, the conductor and a section of wire near the midpoint are crimped together within a tubular crimping member 20 shown in section 1. The remaining exposed areas of the terminus of conductor 14 and the midpoint is insulated by nonconductive adhesive material 23. Alternately, the conductor 14 may be welded to the member 20 to provide a strong electrical connection.

The member 20 is shown in FIG. 1 with an encapsulating sleeve 26 which extends over a portion of the insulating material 15 and to the insulating adhesive material 23. This sleeve 26 may be of a material identical to that of the insulating material 15 and functions to insulate the crimping member 20 while providing a stress relief for the connection between the electrode 12 and the conductor 14. Also shown in FIG. 1 are pincer insulating members 27 and 28 which extend from the sleeve 26 over the portion of the pincers 17 and 18, respectively. These insulating members function to increase the current density at the interface between the electrode 12 and the body organ to which it is connected by reducing the effective conductive surface area of the electrode 12. Of course, in some situations current density control may not be critical or may be within an optimum range without insulating members 27 and 28. Therefore, it is to be understood that the insulating members 27 and 28 are optional on the construction of the electrode 12, their use being dependent upon placement of the electrode and its intended use, among other things.

The uninsulated free ends of the pincers 17 and 18 may terminate in cutting surfaces and may be dimensioned to pierce a fold of body tissue and to touch or overlap one another.

Referring now to FIG. 2, there is depicted a preferred embodiment of the insertion tool 30 used in the attachment of the lead 10 of FIG. 1 to a fold of a body organ. In FIG. 3, a cross sectional view along the lines A—A of the insertion tool of FIG. 2 is depicted. The insertion tool 30 of FIGS. 2 and 3 may be of unitary construction preferably manufactured by injection molding of an insulating plastic material, such as an acetyl homopolymer or copolymer thermoplastic. Insertion tool 30 comprises first means for securely gripping the first and second spaced organ engaging pincers 17 and 18 of the lead of FIG. 1 and second means for applying compressive force on the first and second spaced organ engaging pincers 17 and 18 to mechanically deform them. The first mentioned means comprises the grooves 31 and 32, respectively, located in the inner, opposite planer surfaces of the jaws 36 and 37 of the tool 30. The second means includes the circular bores 33 and 34 extending through the jaws 36 and 37 which are engageable by the tip members or jaws of a forceps or other compression tool. A third means comprising stop member 35 is provided to limit the extent of deformation of the first and second pincers 17 and 18 in a manner to be described more completely hereinafter.

As depicted in FIG. 2, the insertion tool 30 is generally C-shaped having two first and second elongated portions or jaws 36 and 37, respectively. An arcuate portion 38 joins the elongated portions 36 and 37 together. By reference to FIG. 3, it will be noted that the insertion tool 30 is of a uniform thickness except at the free ends of the jaws 36 and 37. At the free ends, the jaws 36 and 37 are tapered so that thickness reduces gradually to half that at the coupling portion 38.

The tapered surfaces 38' of the jaws 36 and 37 provide a clearer view of the pincers 17 and 18 during the attachment procedure. It will be appreciated that the tapered surfaces 38' may appear on both sides of the jaws 36 and 37 in other embodiments thereof.

In the inner surfaces of the free ends of the first and second portions 36 and 37 there are located, as mentioned before, the grooves 31 and 32, respectively. As shown in FIG. 2, these grooves are arcuate and conform to the arc of the pincers 17 and 18 of the lead 10. As shown in FIG. 3, the arcuate grooves 31 and 32 have a predetermined width that is dimensioned to provide frictional engagement with the pincers 17 and 18. The grooves 31 and 32 have a normal, relaxed, spacing apart that is slightly less than that of the outer surfaces of the first and second pincers 17 and 18, so that the pincers are securely gripped by the tool 30 in their open position.

The thickness of the insertion tool 30 is selected to provide an offset space for the stop member 35 and the gripping means 31 and 32, and so that the sleeve 26 of the lead 10 may be accommodated in the space between the jaws 36 and 37. In addition, the dimensions including the thickness of the insertion tool are designed to provide sufficient strength to conduct force exerted on the insertion tool 30 directly to the pincers 17 and 18.

Referring now to FIG. 4, there is shown in perspective a view of the lead 10 securely placed in the insertion tool 30. As shown in FIG. 4, the pincers 17 and 18 have been manually pressed into the grooves 31 and 32, and the electrode 12 is supported by the insertion tool 30. The portion of the lead 10 including the sleeve 26 remains loosely in the space between the jaws 36 and 37 and the conductor 15 exits from the insertion tool 30 along one side of the arcuate portion 38.

Referring now to FIG. 5, there is depicted a standard thoracic instrument such as a right angle forceps 40 (Mueller Model CH-1725 tonsil forceps, for example) with its jaws 41 and 42 inserted into the holes 33 and 34, respectively, of the insertion tool depicted in FIGS. 2–4. The right angle forceps 40 may be used both to place the lead 10 into the grooves of the insertion tool and is intended to be used to exert force upon the pincers 17 and 18 to mechanically deform them about or through a fold of body tissue.

The lead 10 is placed upon the insertion tool 30 by inserting the jaws of the forceps 40 into the two holes 33 and 34 and applying a slight opening pressure on the forceps 40 which in turn will spread the jaws 36 and 37 of the insertion tool 30 apart slightly. At this time, the lead 10 can be placed in the insertion tool 30 by visually aligning the pincers 17 and 18 with the grooves 31 and 32, respectively. Slowly releasing the pressure of the forceps 40 allows the insertion tool 30 to return to its free state. The lead 10 will now be held in place as shown in FIG. 4. When inserting the lead 10 into the insertion tool 30, care should be taken to avoid damaging the silicone rubber insulation 27 and 28, if any, of FIG. 1.

To apply the lead to a fold of body tissue, the forceps jaws 41 and 42 are again inserted into the holes 33 and 34 of the insertion tool 30. In FIG. 5, a right angle forceps 40 is depicted. In the actual use of the device, a forceps should be selected that will give the best view and most comfortable angle of approach to the fold of body tissue selected for attachment to the lead 10. As depicted in FIG. 5, the forceps 40 is preferably inserted into the holes 33 and 34 from the side of the insertion tool 30 possessing the tapered surfaces 38'; so that a clear view of the pincers 17 and 18 may be retained during insertion. Light pressure should be exerted on the forceps 40 to prevent the insertion tool 30 from dropping off the jaws 41 and 42. Alternatively, if the forceps jaws 41 and 42 are tapered, the tool 30 may be pressed onto the tapered jaws in the manner depicted.

While holding the folded body tissue, such as the atrial appendage of the heart with a convenient forceps or clamp, the surgeon is expected to slip the fold of tissue between the opened pincers 17 and 18 at the desired site of electrode placement. Thereupon while holding the tissue in place, the surgeon closes the forceps 40 until a moderate force, resulting from the engagement of the stop member 35 with the portion 37 of the insertion tool 30, is felt. At this point, the first and second pincers 17 and 18 should be fully closed and attached to the folded body tissue. The surgeon then reopens the forceps 40 to spread apart the jaws of the insertion tool 30 to remove it from the electrode 12. The distal portion of the lead 10 should be inspected for proper closure of the pinces 17 and 18. Lead placement should now be complete and electrical measurements taken to insure that proper stimulation or sensing thresholds have been achieved.

If thresholds are too high, the lead can be removed by inserting a closed forceps into the exposed portion of the electrode between the pincers 17 and 18 and then opening the forceps only enough to spread the pincers 17 and 18 far enough apart to withdraw the folded body tissued. The correct opening of the jaw pincers 17 and 18 may be measured by slipping the pincers 17 and 18 over the arcuate portion 38 of the insertion tool 30. The lead must be adjusted to this dimension before attempting to re-insert it.

While not shown in the drawings, a length of string may be attached to the arcuate portion 38, so that the tool 30 may be withdrawn from the incision in case it slips off the jaws of the forceps.

When the lead of the present invention is attached to the atrium or atrial appendage, the pincers will perforate the heart wall. Inasmuch as these chambers are low pressure, there will be no excessive bleeding, the punctures being very analogous to those occurring in the prior art suturing techniques. When the electrode is applied to the ventricle, the thickness of the ventricle wall will prevent a perforation. Again, wherever the electrode is to be placed there must be some penetration.

The combination of the insertion tool 30 and the lead 10 provides more reliability and versatility for application of the lead 10 to body tissue. In the absence of the insertion tool 30, the use of conventionally available forceps or surgical clip applicators, such as that depicted in U.S. Pat. No. 3,777,538 has resulted in unreliable and difficult placement and attachment of the lead 10 to body tissue. Slippage usually occurs between the applicating tool or forceps and the pincers 17 and 18 of the electrode 12. In addition, either too little or too much force may be applied to the pincers 17 and 18 through use of the conventional instruments, resulting in unreliable attachments of the lead 10.

These and other advantages of the invention may be realized in alternate embodiments of the insertion tool. While not expressly depicted herein, it will be realized that the insertion tool 30 could take other shapes and forms that allow for the secure attachment of the electrode 12 to the applicator tool and for the application of force to the pincers 17 and 18. For example, the outer surfaces of the insertion tool of FIG. 2 could include arcuate ribs between which the forceps jaws 41 and 42 might be placed. In addition, the stop member 35 could take the shape of two members rising from both inner surfaces of the jaws 36 and 37.

Obviously many modifications and variations of the present invention are possible on light of the above teachings. For example, while stress considerations indicate that an arcuate pincer configuration is most desirable, the pincers may be formed in any nonarcuate configuration capable of the deformation described herein. It is therefore to be understood that within the scope of the appended claims, the invention may be practiced otherwise as is specifically described.

What I claim is:

1. In combination:
    a body-implantable, electrode carrying lead of the type which is adapted for electrical connection to a remote electrical device having a length of flexible insulated electrical conductor, and conductive first and second pincer means connected to one end of said conductor having free ends for engaging a fold of body tissue, said first and second pincer means being mechanically deformable from an open position wherein the free ends are in spaced opposing relation to a closed position wherein the free ends engage the fold of body tissue;
    insertion tool means for attaching said first and second pincer means to a fold of body tissue comprising a substantially C-shaped member having first and second elongated jaws having opposite facing inner, planar surfaces extending substantially parallel to one another from a portion of said member interconnecting said elongated jaws to the respective free ends thereof, first means formed in the inner surfaces of said first and second elongated jaws proximal to the free ends thereof for securely gripping the first and second pincer means in their open position, and second means formed along said first and second elongated jaws for receiving mechanical force applied perpendicular to said inner surfaces to apply mechanical force through said first means to said first and second pincer means to deform said first and second pincer means to their closed position;

and compressive applicator means having two opposed and aligned in parallel working members, each working member of the applicator means having releasably attached thereto said second means of said C-shaped member, and handle means for bringing said parallel working members of said applicator means together for applying mechanical force through said C-shaped member to deform said first and second pincer means.

2. The combination of claim 1 wherein said free ends of said first and second pincer means terminate at a cutting surface.

3. The combination of claim 1 wherein said first and second pincer means are generally arcuate.

4. The combination of claim 1 wherein said first and second pincer means comprise a length of wire-like conductor attached at its midpoint to said electrical conductor of said lead and formed arcuately to extend from said midpoint generally away from the longitudinal axis of said lead and to extend along its free ends generally toward the longitudinal axis of said lead, the free ends of said first and second pincer means being in spaced generally opposing relation to each other.

5. The combination of claim 4 wherein the midpoint of said wire-like conductor and the portions extending generally away from the longitudinal axis of said lead are encased in insulating material generally inert to body fluids and tissues.

6. The combination of claim 1 wherein said first means comprises grooves having a predetermined length, width and depth proportional to the like dimensions of said first and second pincer means, said grooves formed along the free ends of the inner surfaces of the first and second jaws.

7. The combination of claim 6 wherein said first and second pincer means are generally arcuate in shape having generally facing free ends and wherein said grooves define arcs conforming to the arcuate shape of the first and second pincer means.

8. The combination of claim 7 wherein said grooves are spaced apart in said inner surfaces less than the spacing of the outer diameters of the arcs of the first and second pincer means in their open position, so that said first and second pincer means are securely gripped in said grooves when inserted therein in their open position.

9. The combination of claim 7 wherein said grooves are dimensioned to engage a portion of said first and second pincer means, so that the free ends of said first and second pincer means may engage a fold of body tissue.

10. The combination of claim 1 wherein said second means comprises a pair of generally cylindrical passages extending through said first and second jaws of said insertion tool means and receiving the working members of said compressive applicator means.

11. The combination of claim 1 further comprising a stop member projecting from at least one of said inner surfaces a predetermined distance such that it will engage the opposite inner surface upon operation of said second means to limit the degree of deformation imparted to said first and second pincer means.

12. The combination of claim 1 further comprising narrowing tapered surfaces at the free ends of said C-shaped member adapted to increase visibility of the free ends of said first and second pincer means.

* * * * *